United States Patent [19]
Pfeil et al.

[11] 4,172,049
[45] Oct. 23, 1979

[54] CONTROL-SOLUTION FOR DIAGNOSTIC DETECTION METHODS FOR SUBSTANCES CONTAINED IN THE URINE

[75] Inventors: Emanuel Pfeil; Helmut Kohl, both of Marburg, Fed. Rep. of Germany

[73] Assignee: Behringwerke Aktiengesellschaft, Marburg, Fed. Rep. of Germany

[21] Appl. No.: 904,993

[22] Filed: May 11, 1978

[30] Foreign Application Priority Data

May 13, 1977 [DE] Fed. Rep. of Germany ....... 2721681

[51] Int. Cl.$^2$ ........................ C09K 3/00; G01N 33/16
[52] U.S. Cl. .................................. 252/408; 23/230 B; 424/2; 424/3
[58] Field of Search ...................... 252/408; 23/230 B; 424/2, 3, 317, 131

[56] References Cited

U.S. PATENT DOCUMENTS

| 2,283,262 | 5/1942 | Kamlet ................................ 252/408 |
| 2,509,140 | 5/1950 | Free ..................................... 252/408 |
| 2,577,978 | 12/1951 | Nicholls et al. ...................... 252/408 |
| 2,990,253 | 6/1961 | Smeby .................................. 252/408 |
| 3,212,855 | 10/1965 | Mast et al. ........................... 252/408 |
| 3,446,596 | 5/1969 | Salivar et al. ........................ 252/408 |
| 3,880,590 | 4/1975 | Ocawa et al. ........................ 252/408 |
| 3,973,439 | 8/1976 | Smith et al. .......................... 252/408 |

OTHER PUBLICATIONS

"The Merck Index," eighth edition, Merck & Co., Inc., N. J., p. 957 (1968).
Henry, R. J., "Clinical Chemistry," Hoeder Med. Div., Harper & Row, pp. 689-698 (1972).

Primary Examiner—Benjamin R. Padgett
Assistant Examiner—T. S. Gron
Attorney, Agent, or Firm—Curtis, Morris & Safford

[57] ABSTRACT

What is disclosed is a standard compositon for the control of diagnostic methods for detecting substances contained in urine, said composition comprising a water-soluble acetylacetonate together with a water-soluble hexanitrocobalt-(III)-salt.

3 Claims, No Drawings

CONTROL-SOLUTION FOR DIAGNOSTIC DETECTION METHODS FOR SUBSTANCES CONTAINED IN THE URINE

The present invention relates to a standard for diagnostic detection methods for substances contained in the urine, which standard may be a solution or may also have the form of a water-soluble powder mixture or dried, preferably lyophilized, form. In particular, the standard contains substitute substances for the ketone as well as the nitrite in urine.

The errors which repeatedly occur in the analyses of urine have increased the requirement for control substances which can be brought along. In particular, rapid diagnostics, such as test strips, must be controlled with regard to their quality for the rapid semi-quantitative determination of the urine status. The determination of the urine status requires essentially an indication of glucose, protein, ketone, nitrite, and blood- and pH-value, which are just the most important to be mentioned here.

The sensitivity of the diagnostic agents for determining the aforementioned components to external influences such as, for example, atmospheric moisture and temperature, makes necessary controlling these agents with regard to their functionality. Therefore, a control solution is needed, which behaves in analyses as does urine itself, at least with regard to some components of urine.

The attempt has been made to use so-called control-urines. Lyophilized urine is partly used in which unstable substances have been replaced by chemically stable equivalents.

Although the detection of nitrite in the urine is of great importance as a proof of the presence of nitrite-forming bacteria, this field has been neglected in control-urines. The known control-urines show a similar deficiency with regard to their content of ketone bodies.

The addition of nitrite to liquids or to products to be dissolved, which should simulate various components of the urine, has proved not to be realizable. Inorganic nitrites are known to be unstable.

The same applies to ketone bodies. Acetone is suitable only for control-urines which are kept in liquid form. Lyophilization of acetone-containing material is impossible owing to its volatility. As a constituent of a dry, water-soluble powder, acetone is unsuitable.

In addition to the instability of some components of urine, or of the substituents taken into consideration, it must be taken into account that ineractions of the components have to be excluded in order not to impair the result of the analysis obtained by the mixture.

The goal of the invention was to prepare a urine substitute for the control of diagnostic urinalyses, in particular to find substitutes for ketone bodies and nitrites.

This goal has been achieved by using as a substitute for ketone bodies a water-soluble acetyl acetonate and as a substitute for nitrite a water-soluble hexanitrocobaltate-(III)-salt.

The object of the invention is a control-standard for diagnostic detection methods for substances contained in urine, which standard may be in solution form and may also be present in the form of a powder mixture soluble in water or in dried form, for example in lyophilized form, characterized in that it contains a water-soluble acetylacetonate and/or a water-soluble hexanitritocobaltate-(III)-salt.

Acetylacetonates in the sense of the invention are all water-soluble salts of acetylacetone. The aluminum salt is preferred. The acetylacetonates of the invention show the required analytical properties as substitutes for ketones such as acetone or acetoacetic acid. As lyophilized agents, acetylacetonates are readily reconstituted. The lyophilizates have a good stability on storage. Even after storage for one year at room temperature, the salts of acetylacetone react with sodium nitroprusside as well as is required for freshly prepared ketone-containing solutions.

The concentration of the acetylacetonates in solution should be 10 to 300 mg/100 ml, preferably 50 to 150 mg/100 ml.

Nitrite substitutes in the sense of the invention are water-soluble salts of hexanitrocobaltate-(III), for example the sodium-, lithium-, potassium-, ammonium-, calcium-, strontium-, magnesium- or barium-salts; furthermore the salts with organic bases such as methylamine or guanidine. The sodium salt is preferred.

When using the compounds of this invention as nitrite substitutes, it was found that, surprisingly, the detection reaction for nitrite persisted over a prolonged period of time also in the presence of a primary aromatic amine. The same applied to the lyophilized material. In addition, it was found that hexanitrocobaltate imparts a desirable natural yellow color to the artificial control urine and makes possible a better comparability with natural urine.

The concentration of the hexanitrocobaltates should amount to 0.1 to 300 mg/100 ml, preferably 1 to 10 mg/100 ml.

In addition to acetylacetonate and/or hexanitritocobaltate, the control-solutions or lyophilzates according to the invention may also contain other components, particularly those which are usual and known in urine substitutes. Among these are, for example, hexoses such as glucose or galactose; proteins, such as albumin, globulins or also Bence-Jones-proteins; reducing compounds such as ascorbic acid; buffer salts; urea or uric acid; substances such as erythrocytes which act as peroxidases; hormones; steroids; trace elements; and, if desired also dyestuffs, in particular gall dyestuffs. Furthermore, there are among these also control-solutions, dry powders or lyophilizates, which contain certain additional compounds for the detection of medicaments, drugs or poisons. The same applies to the powder mixtures of the invention to the extent that the aforementioned constituents are solid substances.

The following examples illustrate the invention:

EXAMPLE 1

In 100 ml of a 0.1 m phosphate buffer, pH 6, there were dissolved:
100 mg of glucose
75 mg of albumin from human serum
75 mg of aluminum acetylacetonate
75 mg of N-napthylethylenediamine-dihydrochloride
1 mg of sodium hexanitrocobaltate The ochre colored solution was filtered and lyophilized according on known processes.

The lyophilizate was found to be stable to storage for at least 6 months. For reconstitution, it can be redissolved with 100 ml of water. In this solution, ketone and nitrite can be proved clearly and distinctly, in addition to the other components, with the corresponding reagent test strips as in natural urine.

EXAMPLE 2

0.5 g of disodium hydrogen phosphate 12 $H_2O$
1.35 g of sodium dihydrogen phosphate 2 $H_2O$
0.15 g of glucose
0.05 g of albumin from bovine serum
0.05 g of aluminum acetylacetonate
0.005 g of N-phenyl-1-naphthylamine-8-sulphonic acid and
0.001 g of sodium hexanitrocobaltate.

The components are thoroughly mixed and stored in dry state.

Even after a storage time of 6 months, the control-urine still dissolved in 100 ml of water.

The individual components can be determined distinctly. Ketone and nitrite can be detected with the respective reagent test strips as in natural urine.

We claim:

1. A standard solution for the control of diagnostic methods for detecting substances contained in urine, said solution comprising predetermined amounts of a water-soluble acetylacetonate and a water-soluble hexanitrocobalt-(III)-salt dissolved in a predetermined amount of water.

2. A mixture in the form of a dry powder for reconstitution with water in preparation of a standard solution for the control of diagnostic methods for detecting substances contained in urine, said mixture comprising predetermined amounts of a water-soluble acetylacetonate and a water-soluble hexanitrocobalt-(III)-salt.

3. The mixture as in claim 2, wherein said dry powder is a lyophilizate.

* * * * *